(12) United States Patent
Ahn

(10) Patent No.: US 11,107,215 B2
(45) Date of Patent: Aug. 31, 2021

(54) MEDICAL IMAGE DIAGNOSIS ASSISTANT APPARATUS AND METHOD FOR GENERATING EVALUATION SCORES FOR PLURALITY OF MEDICAL IMAGE DIAGNOSIS ALGORITHMS

(71) Applicant: INFINITE HEALTHCARE CO., LTD., Seoul (KR)

(72) Inventor: Chung Il Ahn, Seoul (KR)

(73) Assignee: INFINITT HEALTHCARE CO., LTD., Seoul (KR)

( * ) Notice: Subject to any disclaimer, the term of this patent is extended or adjusted under 35 U.S.C. 154(b) by 97 days.

(21) Appl. No.: 16/714,141

(22) Filed: Dec. 13, 2019

(65) Prior Publication Data
US 2020/0202523 A1 Jun. 25, 2020

(30) Foreign Application Priority Data
Dec. 21, 2018 (KR) .................. 10-2018-0167136

(51) Int. Cl.
G06K 9/00 (2006.01)
G06T 7/00 (2017.01)
(Continued)

(52) U.S. Cl.
CPC .......... *G06T 7/0012* (2013.01); *G06K 9/6227* (2013.01); *G06K 9/6253* (2013.01);
(Continued)

(58) Field of Classification Search
CPC .. G16H 50/20; G16H 50/30; G06K 2209/051; G06K 9/6227; G06K 9/6253;
(Continued)

(56) References Cited

U.S. PATENT DOCUMENTS 8,879,813 B1 * 11/2014 Solanki .................. A61B 3/14
382/128
9,536,054 B1 * 1/2017 Podilchuk ............ G06T 7/0012
(Continued)

FOREIGN PATENT DOCUMENTS

KR 10-1811028 B1 12/2017
KR 10-1818074 B1 1/2018
(Continued)

*Primary Examiner* — Hadi Akhavannik
(74) *Attorney, Agent, or Firm* — Nelson Mullins Riley & Scarborough LLP; Kongsik Kim, Esq.

(57) ABSTRACT

Disclosed are a medical image diagnosis assistant apparatus and method. The diagnosis assistant apparatus includes a computing system includes a processor. The computing system stores a plurality of medical image diagnosis algorithms each having the diagnostic function of a medical image in memory or a database. The processor extracts a diagnosis requirement for a medical image by analyzing the medical image, selects a plurality of diagnosis application algorithms based on the diagnosis requirement to analyze the medical image from among the plurality of medical image diagnosis algorithms, stores a plurality of diagnosis
(Continued)

results for the medical image associated with each of the plurality of diagnosis application algorithms in the memory or database inside the computing system, and generates evaluation scores for the plurality of medical image diagnosis algorithms.

16 Claims, 2 Drawing Sheets

(51) Int. Cl.
| | |
|---|---|
| *G16H 30/40* | (2018.01) |
| *G16H 50/20* | (2018.01) |
| *G06T 7/70* | (2017.01) |
| *G06K 9/62* | (2006.01) |

(52) U.S. Cl.
CPC ............ *G06K 9/6263* (2013.01); *G06T 7/70* (2017.01); *G16H 30/40* (2018.01); *G16H 50/20* (2018.01); *G06K 2209/051* (2013.01); *G06T 2200/24* (2013.01); *G06T 2207/20084* (2013.01); *G06T 2207/20092* (2013.01); *G06T 2207/30096* (2013.01)

(58) Field of Classification Search
CPC . G06K 9/6263; G06K 2209/05; G06K 9/6271
See application file for complete search history.

(56) References Cited

U.S. PATENT DOCUMENTS

| | | | | |
|---|---|---|---|---|
| 9,779,492 | B1* | 10/2017 | Garnavi | G06N 3/0454 |
| 10,521,705 | B2* | 12/2019 | Lu | G06K 9/6256 |
| 2014/0101080 | A1* | 4/2014 | Lee | G06N 20/00 |
| | | | | 706/12 |
| 2016/0350919 | A1* | 12/2016 | Steigauf | G06K 9/6263 |
| 2016/0364857 | A1* | 12/2016 | Reicher | G06K 9/66 |
| 2017/0061087 | A1* | 3/2017 | Boroczky | G06F 16/24578 |
| 2017/0330319 | A1 | 11/2017 | Xu et al. | |
| 2019/0295440 | A1* | 9/2019 | Hadad | G06F 40/216 |

FOREIGN PATENT DOCUMENTS

| | | |
|---|---|---|
| KR | 10-1929752 B1 | 12/2018 |
| WO | 2017-165801 A1 | 9/2017 |
| WO | 2018-015414 A1 | 1/2018 |
| WO | 2018-031919 A1 | 2/2018 |
| WO | 2018-060723 A1 | 4/2018 |

\* cited by examiner

MEDICAL IMAGE DIAGNOSIS ASSISTANT APPARATUS AND METHOD FOR GENERATING EVALUATION SCORES FOR PLURALITY OF MEDICAL IMAGE DIAGNOSIS ALGORITHMS

CROSS-REFERENCE TO RELATED APPLICATION

This application claims under 35 U.S.C. § 119(a) the benefit of Korean Patent Application No. 10-2018-0167136 filed on Dec. 21, 2018, which is incorporated herein by reference.

TECHNICAL FIELD

The present invention relates to an apparatus and method for assisting the diagnosis for a medical image by means of an automated system. More specifically, the present invention relates to a method for generating evaluation scores for artificial intelligence-based medical image diagnosis algorithms and assisting the diagnosis for a medical image based on the evaluation scores and an apparatus for performing the method.

The present invention was derived from the research conducted as part of the Fundamental SW Computing Technology Development Project sponsored by the Korean Ministry of Science and ICT and the Institute for Information and Communications Technology Promotion [Project Management Number: 2018-0-00861; and Project Name: Development of Intelligent SW Technology for Analysis of Medical Data].

BACKGROUND ART

Technologies for segmenting or detecting objects in an image or classifying objects in an image are used for various purposes in image processing. In a medical image, objects in the image are segmented, detected, and classified based on the brightness or intensity values of the image, in which case each of the objects may be an organ of a human body, or a lesion.

Recently, the introduction of deep learning and a convolutional neural network (CNN) as artificial neural networks in the automation of an image processing process has dramatically improved the performance of an automated image processing process.

However, on the other hand, the insides of recent artificial neural networks, such as deep learning and a CNN, approximate black boxes, and thus there is reluctance for a user to fully accept and adopt them even when acquired results are excellent. In particular, reluctance to artificial neural networks stands out as being more important in the medical imaging field in which human life is dealt with.

Research into explainable artificial intelligence (X-AI) has been attempted in the Defense Advanced Research and Planning (DARPA) of the U.S., etc. (see https://www.darpa.mil/program/explainable-artificial-intelligence). However, no noteworthy results have yet been revealed.

In the medical field, as a technique for segmenting, detecting, classifying and diagnosing lesions having complex shapes, a technique for selectively applying a plurality of segmentation algorithms is disclosed in International Publication No. WO2018/015414 entitled "METHOD AND SYSTEM FOR ARTIFICIAL INTELLIGENCE BASED MEDICAL IMAGE SEGMENTATION."

In the related prior document, a technique of comparing pre-trained segmentation algorithms and selecting at least one of the pre-trained segmentation algorithms is applied to acquire a final result of image segmentation.

However, descriptive information (explanation) about what is the criterion for the selective application of the segmentation algorithms cannot be derived from the related art document, and thus a problem arises in that it is difficult to increase a clinician's confidence in how useful this segmentation technique is clinically.

A similar problem is still present in the process of analyzing a medical image in that it is difficult to have clinical confidence in a process in which an artificial intelligence-based diagnosis system that operates entirely like a black box generates a result.

SUMMARY OF THE DISCLOSURE

Recently, efforts have been made to improve the performance of image segmentation, object detection and object classification techniques by applying deep learning-based artificial intelligence techniques. However, in the case of deep learning-based artificial intelligence, the fact that there is a black box that prevents a user from determining whether or not a result provided from an operation accidentally exhibits high performance and whether or not a determination process appropriate for a corresponding task has been passed through limits the applicability of the deep learning-based artificial intelligence.

In contrast, the use of rule-based training or learning, which is easy to explain, is limited in that better performance cannot be achieved than deep learning. Accordingly, deep learning-based artificial intelligence that can be provide descriptive information or explainable information while having improved performance is being actively researched. In the practical application of image processing using an artificial neural network, descriptive information about the basis of diagnosis and classification is required particularly in the medical imaging field. However, in the related art, descriptive information cannot be derived.

Even in the above-described related art document (International Publication No. WO2018/015414), it is not possible to derive descriptive information (explanation) on which factors affect the improvement of final segmentation performance, and there is no way to verify that clinically significant feedback has been actually and appropriately applied to the deep learning system even when a clinician provides the clinically significant feedback.

An object of the present invention is to provide evaluation scores, including confidence and accuracy scores, for a plurality of medical image diagnosis algorithms in a process in which a user reads a medical image, thereby improving the accuracy of a medical image diagnosis result obtained by the user.

An object of the present invention is to provide recommended information as descriptive information in a process in which a user derives a final diagnosis result by using artificial intelligence medical image diagnosis algorithms, and to allow for the user to provide information about the clinical usefulness of medical image diagnosis algorithms as quantified information.

In accordance with an aspect of the present invention, there is provided a medical image diagnosis assistant apparatus for assisting the diagnosis for a medical image, the diagnosis assistant apparatus including a computing system, wherein the computing system includes a processor, and wherein the computing system is configured to store a plurality of medical image diagnosis algorithms each having a diagnostic function of a medical image in memory or a database.

The processor is configured to extract a diagnosis requirement for a medical image by analyzing the medical image. The processor is further configured to select a plurality of diagnosis application algorithms based on the diagnosis requirement to analyze the medical image from among the plurality of medical image diagnosis algorithms. In this case, the plurality of diagnosis application algorithms includes at least a first diagnosis algorithm and a second diagnosis algorithm. The processor is further configured to, when a plurality of diagnosis results for the medical image is generated by applying each of the plurality of diagnosis application algorithms to the medical image, store the plurality of diagnosis results for the medical image associated with each of the plurality of diagnosis application algorithms in the memory or database inside the computing system. In this case, the plurality of diagnosis results includes at least a first diagnosis result based on the first diagnosis algorithm and a second diagnosis result based on the second diagnosis algorithm. The processor is further configured to generate evaluation scores for the plurality of medical image diagnosis algorithms.

The processor may be further configured to generate display information including evaluation scores for each of the plurality of diagnosis application algorithms and the plurality of diagnosis results, and to provide a user menu that enables a user to select one or more of the plurality of diagnosis application algorithms.

The processor may be further configured to display the first diagnosis result and the second diagnosis result for suspicious lesion locations within the medical image so that the first diagnosis result and the second diagnosis result are compared with each other, and to generate a first diagnosis report based on the first diagnosis result for the suspicious lesion locations within the medical image and a second diagnosis report based on the second diagnosis result therefor.

The processor may be further configured to generate first diagnosis reason image information including information about suspicious lesion locations within the medical image associated with the first diagnosis result and second diagnosis reason image information including information about suspicious lesion locations within the medical image associated with the second diagnosis result, and to generate a first diagnosis report based on the first diagnosis reason image information and the first diagnosis result and a second diagnosis report based on the second diagnosis reason image information and the second diagnosis result.

The processor may be further configured to select the first diagnosis result and the second diagnosis result from among the plurality of diagnosis results as recommended diagnosis results based on the evaluation scores, and to generate display information including the evaluation score for the first diagnosis algorithm, the first diagnosis result, the evaluation score for the second diagnosis algorithm, and the second diagnosis result.

The processor may be further configured to generate confidence scores for each of the plurality of medical image diagnosis algorithms, accuracy scores for each of the plurality of medical image diagnosis algorithms and evaluation confidence scores for each of the plurality of medical image diagnosis algorithms by the user as detailed evaluation objective based on the plurality of diagnosis results and feedback on the plurality of diagnosis results by the user, and to generate the evaluation scores based on the detailed evaluation objectives.

The processor may be further configured to assign weights to the confidence scores for each of the plurality of medical image diagnosis algorithms, the accuracy scores for each of the plurality of medical image diagnosis algorithms and the evaluation confidence scores for each of the plurality of medical image diagnosis algorithms by the user, the confidence scores, the accuracy scores, and the evaluation confidence scores are included in the detailed evaluation objectives, and to update the weights for each of the detailed evaluation objectives so that the weights for each of the detailed evaluation objectives are adjusted according to a target requirement based on the plurality of diagnosis results and the feedback on the plurality of diagnosis results by the user.

The processor may be further configured to extract the diagnosis requirement for the medical image based on an image segmentation result for the medical image, a clinical order for the medical image, and personal information about the examinee of the medical image, and to select the plurality of diagnosis application algorithms to analyze the medical image based on at least one of suitability for the diagnosis requirement and the evaluation scores for each of the plurality of medical image diagnosis algorithms.

The processor may be further configured to generate detailed evaluation objectives for each diagnosis requirement, including information about the type of organ, the location of a lesion, and the relative locations of the organ and the lesion for the diagnosis requirement, based on image segmentation and processing results for the medical image, and to generate the evaluation scores for each of the plurality of medical image diagnosis algorithms with respect to each of the detailed evaluation objectives for the diagnosis requirement.

The processor may be further configured to generate confidence scores for each of the plurality of medical image diagnosis algorithms, accuracy scores for each of the plurality of medical image diagnosis algorithms and evaluation confidence scores for each of the plurality of medical image diagnosis algorithms by the user as detailed evaluation objective based on the plurality of diagnosis results and feedback on the plurality of diagnosis results by the user, and to select the plurality of diagnosis application algorithms based on the correlation between the detailed evaluation objective for the diagnosis requirement and a corresponding one of the detailed evaluation objectives.

The plurality of medical image diagnosis algorithms may be artificial intelligence algorithms using artificial neural networks, and the processor may be further configured to generate the evaluation scores for the diagnosis requirement as pieces of descriptive information for each of the plurality of medical image diagnosis algorithms.

In accordance with another aspect of the present invention, there is provided a medical image diagnosis assistant method, the medical image diagnosis assistant method being performed by a processor inside a computing system for assisting the diagnosis for a medical image and being executed based on program instructions loaded into the processor.

The medical image diagnosis assistant method includes: receiving a medical image; extracting an diagnosis requirement for the medical image based on the diagnosis requirement by analyzing the medical image; selecting a plurality of diagnosis application algorithms to analyze the medical image from among a plurality of medical image diagnosis algorithms stored in memory or a database inside the computing system and each having a diagnostic function of a medical image, wherein the plurality of diagnosis application algorithms comprises at least a first diagnosis algorithm and a second diagnosis algorithm; when a plurality of diagnosis results for the medical image are generated by applying each of the plurality of diagnosis application algorithms to the medical image, storing the plurality of diagnosis results for the medical image associated with each of the plurality of diagnosis application algorithms in the memory or database inside the computing system, wherein the plurality of diagnosis results comprises at least a first diagnosis result based on the first diagnosis algorithm and a second diagnosis result based on the second diagnosis algorithm; and generating evaluation scores for the plurality of medical image diagnosis algorithms.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Figure 1:
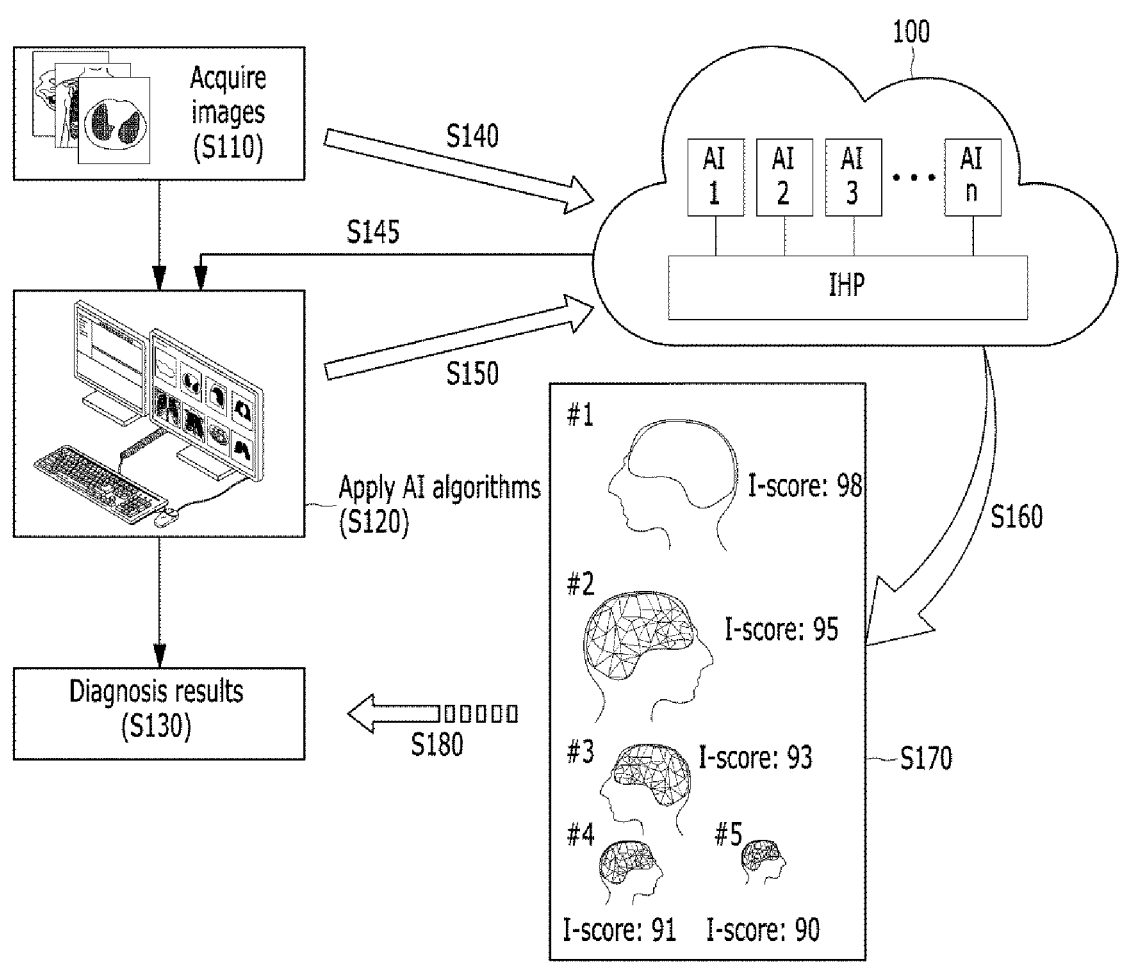
FIG. 1 is a conceptual diagram showing an overall workflow including a medical image diagnosis assistant apparatus according to an embodiment of the present invention.

Embodiments of the present invention will be described in detail below with reference to the accompanying drawings. In the following description, when it is determined that a detailed description of a known component or function may unnecessarily make the gist of the present invention obscure, it will be omitted.

When recently rapidly developed deep learning/CNN-based artificial neural network technology is applied to the imaging field, it may be used to identify visual elements that are difficult to identify with the unaided human eye. The application of this technology is expected to expand to various fields such as security, medical imaging, and non-destructive inspection.

For example, in the medical imaging field, there are cases where cancer tissue is not immediately diagnosed as cancer during a biopsy but is diagnosed as cancer after being tracked and monitored from a pathological point of view. It is difficult for the human eye to confirm whether or not corresponding cells are cancer in a medical image, but there is an expectation that the artificial neural network technology can provide a more accurate prediction than the human eye.

However, although the artificial neural network technology can yield better prediction, classification, analysis, and diagnosis results than the human eye in some studies, there is a lack of descriptive information about the prediction, classification, analysis, and diagnosis results acquired through the application of the artificial neural network technology, and thus a problem arises in that it is difficult to accept and adopt the above results in the medical field.

The present invention has been conceived from the intention to improve the performance of the classifying/predicting objects in an image, which are difficult to classify with the unaided human eye, through the application of the artificial neural network technology. Furthermore, even in order to improve the classification/prediction performance of the artificial neural network technology, it is very important to obtain descriptive information about the internal operation that reaches the generation of a final diagnosis result based on the classification/prediction processes of the artificial neural network technology.

The present invention can present the performance indicators and clinical usefulness of a plurality of medical image diagnosis algorithms based on artificial neural networks as quantified indicators. As a result, it is possible to provide descriptive information about a process of obtaining a final diagnosis result based on the classification/prediction processes of the artificial neural network, and it is also possible to provide a reference for the determination of whether or not a human user can adopt the classification, prediction, analysis, and diagnosis results of an artificial neural network.

When the artificial neural networks of the related art are applied to the analysis/diagnosis of medical images, they are overfit only for given tasks, so that statistical accuracy is high but accuracy is low in some clinically important diagnostic points. Many neural networks of the related art are in such a situation, and thus there occur frequent cases where it is difficult for clinicians to have confidence in the analysis/diagnosis results for medical images to which the artificial neural networks are applied. This risk is more obvious in that IBM's Watson Solution, a well-known artificial neural network, exhibits a problem in that it is overfit for patient race information included in learned data and thus it is significantly low in accuracy in the case of the dataset of new race patients.

Therefore, it is very important to provide a route through which quantified indicators regarding whether or not clinicians will accept these analysis/diagnosis results can be provided and clinicians can provide direct feedback on the generation of the quantified indicators while maximally utilizing the excellent analytical/diagnostic potential of the artificial neural networks.

A medical image diagnosis assistant apparatus and method according to embodiments of the present invention will be described in detail below with reference to FIGS. 1 and 2.

FIG. 1 is a conceptual diagram showing an overall workflow including the medical image diagnosis assistant apparatus according to the embodiment of the present invention. Although the partial sequence (steps S110, S120, and S130) of FIG. 1 may pertain to the related art, it is incorporated into the present invention as part of the configuration of the present invention.

Figure 2:
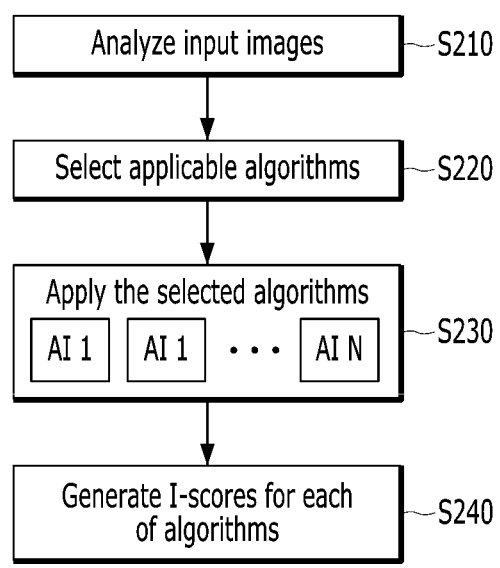
FIG. 2 is an operational flowchart showing a medical image diagnosis assistant method that is performed by the medical image diagnosis assistant apparatus according to an embodiment of the present invention.

FIG. 2 is an operational flowchart showing a medical image diagnosis assistant method that is performed by the medical image diagnosis assistant apparatus according to an embodiment of the present invention.

Referring to FIG. 1, a medical image acquired by a diagnostic imaging apparatus (a modality) at step S110 is transferred to the reading computing terminal of a medical staff and is transferred to a computing system 100 according to the present invention at step S140. The diagnostic imaging apparatus refers to a modality capable of searching for the traces of a lesion within the anatomical structure of a human body or an organ of a human body, such as a CT an MRI, or an ultrasonic diagnosis apparatus, and is not limited to a specific type of apparatus.

The medical image diagnosis assistant apparatus according to the present invention is configured to include the computing system 100, and the medical image diagnosis assistant method according to the present invention is performed by the computing system 100. The computing system 100 includes memory or a database, and also includes a processor. The medical image diagnosis assistant method according to the present invention may be implemented in a form in which program instructions stored in the memory or database are invoked by a processor, are loaded into the processor, and are executed by the processor.

Referring to FIGS. 1 and 2, the computing system 100 analyzes an input medical image at step S210, and a plurality of diagnosis application algorithms to be applied to the diagnosis for a medical image is selected at step S220.

The computing system 100 generates I-scores 170 for each of the plurality of diagnosis application algorithms as evaluation scores at steps S160 and S240. The computing system 100 may generate a plurality of recommended diagnosis results for one examination or at least one medical image at one time.

The computing system 100 may store a plurality of medical image diagnosis algorithms each having a diagnostic function of a medical image in the memory or database. The processor of the computing system 100 extracts a diagnosis requirement for the medical image by analyzing the medical image at step S210. The processor selects the plurality of diagnosis application algorithms based on the diagnosis requirement from among the plurality of medical image diagnosis algorithms to analyze the medical image at step S220.

When the plurality of diagnosis application algorithms is applied to the medical image and a plurality of diagnosis results for the medical image is generated, the processor of the computing system 100 stores the plurality of diagnosis results for the medical image and each of the plurality of diagnosis application algorithms in the memory or database inside the computing system 100 with the plurality of diagnosis results for the medical image associated with each of the plurality of diagnosis application algorithms. In this case, for ease of description, for example, it is assumed that when the plurality of diagnosis application algorithms includes a first diagnosis algorithm and a second diagnosis algorithm, a first diagnosis result based on the first diagnosis algorithm and a second diagnosis result based on the second diagnosis algorithm are obtained.

The processor of the computing system 100 generates I-scores 170 for each of the plurality of diagnosis application algorithms as evaluation scores at steps S160 and S240.

At step S130, diagnosis results are generated using results to which artificial intelligence algorithms are applied by the reading computing terminal of the medical staff at step S120. In this case, the comments of the medical staff may be added in the process S130 of generating a diagnosis result.

In the medical image diagnosis assistant apparatus according to the present invention, the I-scores 170, i.e., evaluation scores, are transferred from the computing system 100 to the reading computing terminal of the medical staff at step S180. Final diagnosis reports may be generated by incorporating the I-scores 170, i.e., evaluation scores, into the generation of the diagnosis results at step S130. According to an embodiment of the present invention, the computing system 100 may generate diagnosis reports together with the I-scores 170, i.e., evaluation scores, and transfer them to the computing system of the medical staff at step S180. In this case, the diagnosis reports generated by the computing system 100 may be written using the diagnosis results based on diagnosis application algorithms having higher I-scores 170, i.e., higher evaluation scores.

The computing system 100 may provide a user interface configured to display a plurality of recommended diagnosis results at one time, to generate the plurality of recommended diagnosis results without requiring the additional operation of a user, and to check/display the plurality of recommended diagnosis results. The processor of the computing system 100 may generate display information including evaluation scores for each of the plurality of diagnosis application algorithms and the plurality of diagnosis results, and may provide a user menu configured to allow for a user to select one or more of the plurality of diagnosis application algorithms.

The computing system 100 provides a system or interface configured to display the comparisons between suspicious body parts for one examination exam or at least one image or to present diagnosis reports in response to a search for a plurality of recommended diagnosis results. The processor of the computing system 100 may display a first diagnosis result and a second diagnosis result for suspicious lesion locations within the medical image so that they can be compared with each other, and may generate a first diagnosis report based on the first diagnosis result for the suspicious lesion locations within the medical image and a second diagnosis report based on the second diagnosis result therefor. In other words, when different diagnosis results are obtained by applying different diagnosis application algorithms to the same medical image, this plurality of diagnosis results are displayed such that they can be compared with each other, and the user may select any one of the first diagnosis result and the second diagnosis result and generate it as a final diagnosis result. In this case, a user interface configured to determine whether or not the user will accept an diagnosis result for each of the suspicious lesion locations presented by the first diagnosis result and the second diagnosis result may be provided, and the accuracies of the first diagnosis result and the second diagnosis result may be compared with each other for each lesion diagnosis result. Information about whether or not the user finally has accepted each of the plurality of automatic diagnosis results for each lesion diagnosis result may be transferred back to the computing system 100 as feedback information, and may be utilized as sub-information that constitutes part of an evaluation score.

The computing system 100 may provide a user interface configured to compare and display diagnosis reason images or diagnosis reports corresponding to the plurality of recommended diagnosis results. The processor of the computing system 100 generates first diagnosis reason image information including information about suspicious lesion locations within the medical image associated with the first diagnosis result and second diagnosis reason image information including information about suspicious lesion locations within the medical image associated with the second diagnosis result, and may generate a first diagnosis report based on the first diagnosis reason image information and the first diagnosis result and a second diagnosis report based on the second diagnosis reason image information and the second diagnosis result. When the first diagnosis result and the second diagnosis result are different for the same suspicious lesion location within the medical image, the user may invoke and compare the first diagnosis reason image information of the first diagnosis result and the second diagnosis reason image information of the second diagnosis result. Since the originals of the base medical images are the same and the regions diagnosed as lesions by each of the diagnosis application algorithms are different from each other, the regions of the originals of the medical images referred to by each of the diagnosis application algorithms as bases for the diagnoses of the lesions may be different from each other in this case. For example, when the diagnosis application algorithms perform a function such as object detection, diagnosis reason image information may be represented as a box including a specific object or information about the contour lines of a specific object. Furthermore, information about the probabilities at which the diagnosis application algorithms have detected the corresponding objects may be included in and generated as diagnosis reason image information.

The computing system 100 may provide a user interface configured to allow for recommended diagnosis results to be selected using I-scores 170, i.e., internally calculated evaluation scores, and to allow for a radiologist to evaluate/check diagnosis confidence in corresponding recommended analyses (e.g., recommended diagnosis algorithms consistent with the diagnosis results of the radiologist) because the evaluation scores are also displayed. The processor of the computing system 100 may select the first diagnosis result and the second diagnosis result from among the plurality of diagnosis results as recommended diagnosis results based on the evaluation scores. The processor may generate display information including the evaluation score for the first diagnosis algorithm, the first diagnosis result, the evaluation score for the second diagnosis algorithm, and the second diagnosis result.

The computing system 100 may generate an evaluation score based on the confidence score of a corresponding diagnosis algorithm, the accuracy score of the diagnosis algorithm, and the evaluation confidence score of a radiologist who provides feedback. The processor may generate the confidence score of each of the plurality of medical image diagnosis algorithms, the accuracy score of the medical image diagnosis algorithm, and the evaluation confidence score of the medical image diagnosis algorithm by the user as detailed evaluation objectives based on a corresponding one of the plurality of diagnosis results and feedback on the diagnosis result, and may generate an evaluation score based on the detailed evaluation objectives.

For example, the criteria for the generation of the evaluation score may be implemented as follows:

$$I\text{-score} = a \times (\text{the confidence score of an AI algorithm}) + b \times (\text{the accuracy score of the AI algorithm}) + c \times (\text{the evaluation confidence score of the AI algorithm by a radiologist}) \quad (1)$$

The confidence score of the algorithm may be given to the algorithm by the radiologist. In other words, when it is determined that the first diagnosis result is more accurate than the second diagnosis result, a higher confidence score may be given to the first diagnosis result.

The accuracy score of the algorithm may be determined based on the extent to which the radiologist accepts the diagnosis result of the algorithm without a separate score giving process. For example, in the case where when the first diagnosis result presents ten suspicious lesion locations, the radiologist approves nine suspicious lesion locations, the accuracy score may be given as 90/100.

Another embodiment in which the accuracy score of the algorithm is given may be a case where an accurate result is revealed through a biopsy or the like. In this case, the accuracy of the diagnosis result of the diagnosis algorithm may be revealed in comparison with the accurate result obtained through the biopsy. When the user inputs the accurate result, obtained through the biopsy, to the computing system 100, the computing system 100 may calculate the accuracy score of the diagnosis algorithm by comparing the diagnosis result with the accurate result obtained through the biopsy (a reference).

The evaluation confidence score of the radiologist may be provided as a confidence score for the evaluation of the radiologist. In other words, when the radiologist is an expert having a loner experience in a corresponding clinical field, a higher evaluation confidence score may be given accordingly. The evaluation confidence score may be calculated by taking into consideration the years of experience of the radiologist, the specialty of the radiologist, whether or not the radiologist is a medical specialist, and the experience in the corresponding clinical field.

The computing system 100 may update evaluation score calculation criteria according to a predetermined internal schedule while continuously learning the evaluation score calculation criteria by means of an internal artificial intelligence algorithm. The processor may assign weights to the confidence scores of each of the plurality of medical image diagnosis algorithms, the accuracy scores of each of the plurality of medical image diagnosis algorithms, and the evaluation confidence scores of each of the plurality of medical image diagnosis algorithms by the user, the confidence score, the accuracy score, and the evaluation confidence scores are included in the detailed evaluation objectives, and may update the weights of the detailed evaluation objectives so that the weights of the detailed evaluation objectives can be adjusted according to a target requirement based on the plurality of diagnosis results and feedback on the plurality of diagnosis results by the user.

An example of the target requirement may be a case where adjustment is performed such that there is a correlation between the confidence of the user in the algorithms and the accuracy of the algorithms. For example, first and second diagnosis algorithms having the same accuracy score may have different confidence scores that are given by a radiologist. In this case, when confidence scores are different from each other while exhibiting a certain tendency after the removal of the general errors of the evaluation of the radiologist, it can be recognized that the confidence of the radiologist in the first diagnosis algorithm is different from the confidence of the radiologist in the second diagnosis algorithm. For example, in the case where the first and second diagnosis algorithms generate accurate diagnosis results at nine of a total of ten suspicious lesion locations, resulting in an accuracy score of 90/100 but only the first diagnosis algorithm accurately identifies a severe lesion and the second diagnosis algorithm does not identify the lesion, the confidence of the radiologist in the first diagnosis algorithm may be different from the confidence of the radiologist in the second diagnosis algorithm. A means for adjusting the correlation between the accuracy and the confidence may be a means for adjusting the weights of each of the detailed evaluation objectives or detailed criteria for the selection of target lesions related to the determination of accuracy. In this case, there may be used a method that classifies lesions according to criteria such as the hardness/severity of an identified lesion, the position of the lesion from the center of a medical image, and the difficulty of identifying the lesion (the difficulty is high in a region where bones, organs, and blood vessels are mixed in a complicated form) and assigns different weights to the diagnosis accuracies of lesions in respective regions.

The computing system 100 may include a function of automatically allocating a plurality of artificial intelligence algorithms that are applicable depending on an image. To determine a plurality of artificial intelligence algorithms applicable to an image, the computing system 100 may classify one examination or at least one image by means of a separate image classification artificial intelligence algorithm inside a diagnosis recommendation system, and may then apply a plurality of artificial intelligence algorithms.

The processor may extract the diagnosis requirement for the medical image based on an image segmentation result for the medical image, a clinical order (request) for the medical image, and personal information about the examinee of the medical image. The processor may select the plurality of diagnosis application algorithms to analyze the medical image based on at least one of suitability for the diagnosis requirement and the evaluation scores for each of the plurality of medical image diagnosis algorithms. In other words, information about a request for the acquisition of the medical image, the details of a suspicious disease accompanying the request, the department of the clinician, and a body part or organ photographed in the medical image, which is transferred from the clinician to the radiologist, may be taken into consideration as the clinical order (request). Furthermore, when each of the diagnosis application algorithms is selected, information about the purpose of diagnosis and the object of diagnosis defined by the artificial intelligence algorithm may be taken into consideration, and also the gender and age of the examinee of the medical image and the severity of a disease may be taken into consideration.

The computing system 100 may subdivide and refine the recommended objectives for the same diagnosis purpose (the same diagnosis requirement) for the same body part while associating an image analysis function and an evaluation score generation function with each other. For example, there may be provided a system capable of recommending an algorithm suitable for the diagnosis of the center of a particular organ, an algorithm suitable for the diagnosis of the periphery of a particular organ, an algorithm suitable for a region where bones, organs, and blood vessels are mixed in a complicated form, etc. in a detailed manner. This function may be implemented via a separate AI algorithm.

The processor may generate detailed evaluation objectives for each diagnosis requirement, including information about the type of organ, the location of a lesion, and the relative locations of the organ and the lesion for each diagnosis requirement, based on image segmentation and processing results for the medical image, and may generate evaluation scores for each of the plurality of medical image diagnosis algorithms with respect to each of the detailed evaluation objectives for each diagnosis requirement.

The computing system 100 may subdivide and refine criteria for the generation of evaluation scores based on image analysis results. For example, an algorithm with high overall accuracy and low confidence may exhibit high overall accuracy but may exhibit low accuracy for a specific objective. In this case, the computing system 100 may specifically select diagnosis objectives that highly affect confidence. In other words, the computing system 100 may refine and subdivide the criteria for the generation of evaluation scores by using the image analysis results.

The processor may generate a confidence score for each of the plurality of medical image diagnosis algorithms, an accuracy score for the medical image diagnosis algorithm, and an evaluation confidence score for the medical image diagnosis algorithm by the user as detailed evaluation objectives based on a corresponding one of the plurality of diagnosis results and feedback on the diagnosis result by the user. The processor may select each of the plurality of diagnosis application algorithms based on the correlation between each detailed evaluation objective for the diagnosis requirement and a corresponding one of the detailed evaluation objectives.

In an embodiment of the present invention, the plurality of medical image diagnosis algorithms may be medical image diagnosis algorithms using artificial neural networks. In this case, the evaluation score and the detailed evaluation objectives may be generated as descriptive information for each diagnosis algorithm, and the computing system 100 may feed the evaluation score and the detailed evaluation objectives back to the creator of the diagnosis algorithm so that the information can be used to improve the diagnosis algorithm. In this case, when each of the artificial neural networks is an artificial neural network using a relevance score and a confidence level, which is being studied recently, an statistical analysis is performed with the evaluation score and the detailed evaluation objectives associated with the relevance score or confidence level of the artificial neural network, and thus the evaluation score and the detailed evaluation objectives may affect the improvement of the diagnosis algorithm.

In an embodiment of the present invention, after the applicable algorithms have been selected by the computing system 100, information about the selected diagnosis application algorithms may be transferred to the reading computing terminal of the medical staff at step S145, and artificial intelligence algorithms (the diagnosis application algorithms) may be actually applied to the medical image in the reading computing terminal of the medical staff at step S120.

In this case, a plurality of diagnosis results obtained by actually applying the plurality of diagnosis application algorithms is transferred to the computing system 100 at step S150. The computing system 100 may store the plurality of diagnosis results and the plurality of diagnosis application algorithms in the memory or database inside the computing system 100 with the plurality of diagnosis results associated with the plurality of diagnosis application algorithms. In this case, the feedback indicators input for the plurality of diagnosis results or the plurality of diagnosis application algorithms via the reading computing terminal of the medical staff by the medical staff may be also fed back to the computing system at step S150. The feedback indicators and the evaluation target, i.e., the plurality of diagnosis results or the plurality of diagnosis application algorithms, are stored in the memory or database inside the computing system 100 with the feedback indicators associated with the plurality of diagnosis results or the plurality of diagnosis application algorithms.

The embodiment of the present invention is designed to provide advantages obtainable by present invention while minimizing the deformation of the medical image diagnosis sequence S110, S120 and S130 of the related art as much as possible.

In another embodiment of the present invention, the computing system 100 may perform the process of selecting a plurality of diagnosis application algorithms and generating a plurality of diagnosis results by applying the plurality of diagnosis application algorithms to a medical image by itself. In this case, the computing system 100 may transfer not only information about the selected diagnosis application algorithms but also the plurality of diagnosis results based on the diagnosis application algorithms to the reading computing terminal of the medical staff at step S145, and the results obtained by applying artificial intelligence algorithms (the diagnosis application algorithms) to the medical image may be displayed on the reading computing terminal of the medical staff at step S120.

In this case, an embodiment of the present invention may provide advantages obtainable by present invention even when the computing power of the reading computing terminal of the medical staff is not high, e.g., the reading computing terminal of the medical staff is a mobile device or an old-fashioned computing system. In this case, in an embodiment of the present invention, an agent that applies the artificial intelligence algorithms to the medical image is the computing system 100, the computing system 100 functions as a type of server, and the reading computing terminal of the medical staff may operate based on a thin-client concept. In this case, in an embodiment of the present invention, the feedback indicators input for the plurality of diagnosis results or the plurality of diagnosis application algorithms via the reading computing terminal of the medical staff by the medical staff may be fed back to the computing system at step S150. The feedback indicators and the evaluation targets, i.e., the plurality of diagnosis results or the plurality of diagnosis application algorithms, may be stored in the memory or database inside the computing system 100 with the feedback indicators associated with the plurality of diagnosis results or the plurality of diagnosis application algorithms.

As described above, in an embodiment of the present invention, step S230 of applying the selected algorithms may be performed in the diagnosis system of the clinician at step S120, and a plurality of diagnosis results may be transferred to the computing system 100 at step S150. In another embodiment of the present invention, overall step S230 of applying the selected algorithms may be performed within the computing system 100 and then the results of the application may be displayed on the diagnosis system of the clinician at steps S145 and S120.

The method of assisting the diagnosis for a medical image according to an embodiment of the present invention may be implemented in the form of program instructions, and may be then recorded in a computer-readable storage medium. The computer-readable storage medium may include program instructions, data files, and data structures solely or in combination. Program instructions recorded on the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand.

According to the present invention, a user may compare the plurality of recommended diagnosis results of a plurality of artificial intelligence medical image diagnosis algorithms applicable to a corresponding image with his or her diagnosis result in the process of analyzing the medical image, thereby increasing the accuracy of the diagnosis result for the medical image by the user.

According to the present invention, a plurality of recommended diagnosis results for parts that may not be identified by a user may be compared with each other and referred to via a plurality of artificial intelligence medical image diagnosis algorithms. The user may verify his or her diagnosis result through comparison with a plurality of diagnosis results via the corresponding system, thereby achieving accurate diagnosis and increasing the confidence of diagnosis.

Furthermore, diagnosis reason images for a plurality of recommended diagnosis results may be referred to in the diagnosis recommendation system, so that the accuracy/confidence of the diagnosis results of a plurality of recommended artificial intelligence medical image diagnosis algorithms similar to the diagnosis result of a user may be evaluated and the user's ability to read/analyze a medical image may be improved.

The evaluation of recommended artificial intelligence algorithms by a user may be related to the charging system of an evaluation system inside the diagnosis recommendation system.

According to the present invention, evaluation scores for artificial intelligence medical image diagnosis algorithms inside the diagnosis recommendation system may be provided as descriptive information, a user may obtain information about the clinical usefulness of medical image diagnosis algorithms in the process of generating a final diagnosis result, and the information about the clinical usefulness may be fed back to the diagnosis recommendation system of the present invention.

The descriptive information that is provided by the present invention may, in turn, be beneficially used to improve the performances and accuracies of medical image diagnosis algorithms based on artificial neural networks.

Although the present invention has been described with reference to specific details, such as the specific components, and the limited embodiments and drawings, these are provided merely to help a general understanding of the present invention, and the present invention is not limited thereto. Furthermore, those having ordinary knowledge and/or skill in the technical field to which the present invention pertains may make various modifications and variations from the above detailed description.

Therefore, the spirit of the present invention should not be defined based only on the described embodiments, and not only the attached claims but also all equivalent to the claims should be construed as falling within the scope of the spirit of the present invention.

What is claimed is:

1. A medical image diagnosis assistant apparatus for assisting a diagnosis for a medical image, the diagnosis assistant apparatus comprising a computing system, wherein the computing system comprises a processor;

wherein the computing system is configured to store a plurality of medical image diagnosis algorithms each having a diagnostic function of a medical image in memory or a database; and wherein the processor is configured to:

extract a diagnosis requirement for a medical image by analyzing the medical image;

select a plurality of diagnosis application algorithms based on the diagnosis requirement to analyze the medical image from among the plurality of medical image diagnosis algorithms, wherein the plurality of diagnosis application algorithms comprises at least a first diagnosis algorithm and a second diagnosis algorithm;

when a plurality of diagnosis results for the medical image are generated by applying each of the plurality of diagnosis application algorithms to the medical image, store the plurality of diagnosis results for the medical image associated with each of the plurality of diagnosis application algorithms in the memory or database inside the computing system, wherein the plurality of diagnosis results comprises at least a first diagnosis result based on the first diagnosis algorithm and a second diagnosis result based on the second diagnosis algorithm;

generate evaluation scores for the plurality of medical image diagnosis algorithms;

extract the diagnosis requirement for the medical image based on an image segmentation result for the medical image, a clinical order for the medical image, and personal information about an examinee of the medical image; and select the plurality of diagnosis application algorithms, to analyze the medical image, based on at least one of suitability for the diagnosis requirement and the evaluation scores for each of the plurality of medical image diagnosis algorithms.

2. The medical image diagnosis assistant apparatus of claim 1, wherein the processor is further configured to:

generate display information, including evaluation scores for each of the plurality of diagnosis application algorithms and the plurality of diagnosis results; and provide a user menu that enables a user to select one or more of the plurality of diagnosis application algorithms.

3. The medical image diagnosis assistant apparatus of claim 1, wherein the processor is further configured to:

display the first diagnosis result and the second diagnosis result for suspicious lesion locations within the medical image so that the first diagnosis result and the second diagnosis result are compared with each other; and generate a first diagnosis report based on the first diagnosis result for the suspicious lesion locations within the medical image and a second diagnosis report based on the second diagnosis result therefor.

4. The medical image diagnosis assistant apparatus of claim 1, wherein the processor is further configured to:

generate first diagnosis reason image information including information about suspicious lesion locations within the medical image associated with the first diagnosis result and second diagnosis reason image information including information about suspicious lesion locations within the medical image associated with the second diagnosis result; and generate a first diagnosis report based on the first diagnosis reason image information and the first diagnosis result and a second diagnosis report based on the second diagnosis reason image information and the second diagnosis result.

5. The medical image diagnosis assistant apparatus of claim 1, wherein the processor is further configured to:

select the first diagnosis result and the second diagnosis result from among the plurality of diagnosis results as recommended diagnosis results based on the evaluation scores; and generate display information including the evaluation score for the first diagnosis algorithm, the first diagnosis result, the evaluation score for the second diagnosis algorithm, and the second diagnosis result.

6. A medical image diagnosis assistant apparatus for assisting a diagnosis for a medical image, the diagnosis assistant apparatus comprising a computing system, wherein the computing system comprises a processor;

wherein the computing system is configured to store a plurality of medical image diagnosis algorithms each having a diagnostic function of a medical image in memory or a database; and wherein the processor is configured to:

extract a diagnosis requirement for a medical image by analyzing the medical image;

select a plurality of diagnosis application algorithms based on the diagnosis requirement to analyze the medical image from among the plurality of medical image diagnosis algorithms, wherein the plurality of diagnosis application algorithms comprises at least a first diagnosis algorithm and a second diagnosis algorithm;

when a plurality of diagnosis results for the medical image are generated by applying each of the plurality of diagnosis application algorithms to the medical image, store the plurality of diagnosis results for the medical image associated with each of the plurality of diagnosis application algorithms in the memory or database inside the computing system, wherein the plurality of diagnosis results comprises at least a first diagnosis result based on the first diagnosis algorithm and a second diagnosis result based on the second diagnosis algorithm;

generate evaluation scores for the plurality of medical image diagnosis algorithms;

generate confidence scores for each of the plurality of medical image diagnosis algorithms, accuracy scores for each of the plurality of medical image diagnosis algorithms and evaluation confidence scores for each of the plurality of medical image diagnosis algorithms by the user as detailed evaluation objective based on the plurality of diagnosis results and feedback on the plurality of diagnosis results by the user; and generate the evaluation scores based on the detailed evaluation objectives.

7. The medical image diagnosis assistant apparatus of claim 6, wherein the processor is further configured to:

assign weights to the confidence scores for each of the plurality of medical image diagnosis algorithms, the accuracy scores for each of the plurality of medical image diagnosis algorithms and the evaluation confidence scores for each of the plurality of medical image diagnosis algorithms by the user, wherein the confidence scores, the accuracy scores, and the evaluation confidence scores are included in the detailed evaluation objectives; and update the weights for each of the detailed evaluation objectives so that the weights for each of the detailed evaluation objectives are adjusted according to a target requirement based on the plurality of diagnosis results and the feedback on the plurality of diagnosis results by the user.

8. A medical image diagnosis assistant apparatus for assisting a diagnosis for a medical image, the diagnosis assistant apparatus comprising a computing system, wherein the computing system comprises a processor;

wherein the computing system is configured to store a plurality of medical image diagnosis algorithms each having a diagnostic function of a medical image in memory or a database; and wherein the processor is configured to:

extract a diagnosis requirement for a medical image by analyzing the medical image;

select a plurality of diagnosis application algorithms based on the diagnosis requirement to analyze the medical image from among the plurality of medical image diagnosis algorithms, wherein the plurality of diagnosis application algorithms comprises at least a first diagnosis algorithm and a second diagnosis algorithm;

when a plurality of diagnosis results for the medical image are generated by applying each of the plurality of diagnosis application algorithms to the medical image, store the plurality of diagnosis results for the medical image associated with each of the plurality of diagnosis application algorithms in the memory or database inside the computing system, wherein the plurality of diagnosis results comprises at least a first diagnosis result based on the first diagnosis algorithm and a second diagnosis result based on the second diagnosis algorithm;

generate evaluation scores for the plurality of medical image diagnosis algorithms;

generate detailed evaluation objectives for each diagnosis requirement, including information about a type of organ, a location of a lesion, and relative locations of the organ and the lesion for the diagnosis requirement, based on image segmentation and processing results for the medical image; and generate the evaluation scores for each of the plurality of medical image diagnosis algorithms with respect to each of the detailed evaluation objectives for the diagnosis requirement.

9. The medical image diagnosis assistant apparatus of claim 8, wherein the processor is further configured to:

generate confidence scores for each of the plurality of medical image diagnosis algorithms, accuracy scores for each of the plurality of medical image diagnosis algorithms and evaluation confidence scores for each of the plurality of medical image diagnosis algorithms by the user as detailed evaluation objective based on the plurality of diagnosis results and feedback on the plurality of diagnosis results by the user; and select the plurality of diagnosis application algorithms based on a correlation between the detailed evaluation objective for the diagnosis requirement and a corresponding one of the detailed evaluation objectives.

10. The medical image diagnosis assistant apparatus of claim 1, wherein:

the plurality of medical image diagnosis algorithms are artificial intelligence algorithms using artificial neural networks; and the processor is further configured to generate the evaluation scores for the diagnosis requirement as pieces of descriptive information for each of the plurality of medical image diagnosis algorithms.

11. A medical image diagnosis assistant method, the medical image diagnosis assistant method being performed by a processor inside a computing system for assisting a diagnosis for a medical image and being executed based on program instructions loaded into the processor, the medical image diagnosis assistant method comprising:

receiving a medical image;

extracting a diagnosis requirement for the medical image by analyzing the medical image;

selecting a plurality of diagnosis application algorithms based on the diagnosis requirement to analyze the medical image from among a plurality of medical image diagnosis algorithms stored in memory or a database inside the computing system and each having a diagnostic function of a medical image, wherein the plurality of diagnosis application algorithms comprises at least a first diagnosis algorithm and second diagnosis algorithm;

when a plurality of diagnosis results for the medical image are generated by applying each of the plurality of diagnosis application algorithms to the medical image, storing the plurality of diagnosis results for the medical image associated with each of the plurality of diagnosis application algorithms in the memory or database inside the computing system, wherein the plurality of diagnosis results comprises at least a first diagnosis result based on the first diagnosis algorithm and a second diagnosis result based on the second diagnosis algorithm;

generating evaluation scores for the plurality of medical image diagnosis algorithms;

extracting the diagnosis requirement for the medical image based on an image segmentation result for the medical image, a clinical order for the medical image, and personal information about an examinee of the medical image; and selecting the plurality of diagnosis application algorithms, to analyze the medical image, based on at least one of suitability for the diagnosis requirement and the evaluation scores for each of the plurality of medical image diagnosis algorithms.

12. The medical image diagnosis assistant method of claim 11, further comprising:

generating display information, including evaluation scores for each of the plurality of diagnosis application algorithms and the plurality of diagnosis results; and providing a user menu that enables a user to select one or more of the plurality of diagnosis application algorithms.

13. The medical image diagnosis assistant method of claim 11, further comprising:

generating display information that visualizes the first diagnosis result and the second diagnosis result for suspicious lesion locations within the medical image so that the first diagnosis result and the second diagnosis result are compared with each other; and generating a first diagnosis report based on the first diagnosis result for the suspicious lesion locations within the medical image and a second diagnosis report based on the second diagnosis result therefor.

14. The medical image diagnosis assistant method of claim 11, further comprising:

generating first diagnosis reason image information including information about suspicious lesion locations within the medical image associated with the first diagnosis result and second diagnosis reason image information including information about suspicious lesion locations within the medical image associated with the second diagnosis result; and generating a first diagnosis report based on the first diagnosis reason image information and the first diagnosis result and a second diagnosis report based on the second diagnosis reason image information and the second diagnosis result.

15. The medical image diagnosis assistant method of claim 11, further comprising:

selecting the first diagnosis result and the second diagnosis result from among the plurality of diagnosis results as recommended diagnosis results based on the evaluation scores; and generating display information, including the evaluation score for the first diagnosis algorithm, the first diagnosis result, the evaluation score for the second diagnosis algorithm, and the second diagnosis result.

16. A medical image diagnosis assistant method, the medical image diagnosis assistant method being performed by a processor inside a computing system for assisting a diagnosis for a medical image and being executed based on program instructions loaded into the processor, the medical image diagnosis assistant method comprising:

receiving a medical image;

extracting a diagnosis requirement for the medical image by analyzing the medical image;

selecting a plurality of diagnosis application algorithms based on the diagnosis requirement to analyze the medical image from among a plurality of medical image diagnosis algorithms stored in memory or a database inside the computing system and each having a diagnostic function of a medical image, wherein the plurality of diagnosis application algorithms comprises at least a first diagnosis algorithm and second diagnosis algorithm;

when a plurality of diagnosis results for the medical image are generated by applying each of the plurality of diagnosis application algorithms to the medical image, storing the plurality of diagnosis results for the medical image associated with each of the plurality of diagnosis application algorithms in the memory or database inside the computing system, wherein the plurality of diagnosis results comprises at least a first diagnosis result based on the first diagnosis algorithm and a second diagnosis result based on the second diagnosis algorithm;

generating evaluation scores for the plurality of medical image diagnosis algorithms;

generating confidence scores for each of the plurality of medical image diagnosis algorithms, accuracy scores for each of the plurality of medical image diagnosis algorithms and evaluation confidence scores for each of the plurality of medical image diagnosis algorithms by the user as detailed evaluation objective based on the plurality of diagnosis results and feedback on the plurality of diagnosis results by the user; and generating the evaluation scores based on the detailed evaluation objectives.

\* \* \* \* \*